(12) United States Patent
Durand

(10) Patent No.: US 7,292,929 B2
(45) Date of Patent: Nov. 6, 2007

(54) SYSTEM FOR A VIRTUAL DEW POINT SENSOR

(75) Inventor: James C. Durand, Dunlap, IL (US)

(73) Assignee: Caterpillar Inc., Peoria, IL (US)

( * ) Notice: Subject to any disclaimer, the term of this patent is extended or adjusted under 35 U.S.C. 154(b) by 41 days.

(21) Appl. No.: 11/393,955

(22) Filed: Mar. 31, 2006

(65) Prior Publication Data

US 2007/0239344 A1    Oct. 11, 2007

(51) Int. Cl.
*B60T 7/12* (2006.01)
*F02B 47/08* (2006.01)

(52) U.S. Cl. .................. 701/108; 123/568.21

(58) Field of Classification Search .............. 701/103, 701/108, 114; 123/568.21, 568.22; 73/116, 73/118.1
See application file for complete search history.

(56) References Cited

U.S. PATENT DOCUMENTS

| | | | |
|---|---|---|---|
| 5,887,651 A * | 3/1999 | Meyer ................... | 165/223 |
| 6,073,480 A | 6/2000 | Gokhfeld | |
| 6,557,771 B2 | 5/2003 | Shah | |
| 6,681,171 B2 | 1/2004 | Rimnac et al. | |
| 6,725,848 B2 | 4/2004 | Ramamurthy et al. | |
| 6,817,197 B1 * | 11/2004 | Padfield ................... | 62/176.6 |
| 6,934,621 B2 | 8/2005 | Bhargava et al. | |
| 6,948,475 B1 | 9/2005 | Wong et al. | |
| 7,007,680 B2 * | 3/2006 | Tussing et al. ......... | 123/568.12 |
| 7,163,005 B2 * | 1/2007 | Tussing et al. ......... | 123/568.12 |
| 2005/0021217 A1 | 1/2005 | Bhargava et al. | |
| 2005/0021218 A1 | 1/2005 | Bhargava et al. | |
| 2006/0016439 A1 * | 1/2006 | Tussing et al. ......... | 123/568.22 |

FOREIGN PATENT DOCUMENTS

GB    2 404 455 A    2/2005

* cited by examiner

*Primary Examiner*—John T. Kwon
(74) *Attorney, Agent, or Firm*—Finnegan, Henderson, Farabow, Garrett & Dunner

(57) ABSTRACT

A system for a virtual dew point sensor is disclosed including a method for operating the virtual dew point sensor. The method includes determining a first humidity ratio indicative of the humidity associated with an ambient air as a function of at least a relative humidity associated with the ambient air. The method also includes determining a second humidity ratio indicative of the humidity associated with an exhaust gas as a function of at least one engine parameter. The method also includes determining a third humidity ratio indicative of combustion air directed toward an inlet manifold of an engine as a function of the first and second humidity ratios. The method further includes determining at least one dew point indicative of the combustion air as a function of the third humidity ratio and a pressure indicative of the combustion air.

20 Claims, 4 Drawing Sheets

SYSTEM FOR A VIRTUAL DEW POINT SENSOR

TECHNICAL FIELD

The present disclosure relates to a system for a virtual dew point sensor system and, more particularly, to a method and apparatus for a virtual dew point sensor.

BACKGROUND

Turbocharged and/or supercharged engine systems typically include a compressor and an air cooler upstream of one or more combustion chambers of an engine. Often, the combustion air comprises a mixture of ambient air and recirculated exhaust gas in an attempt to reduce undesirable emissions produced during combustion. Recirculated exhaust gas often includes considerable amounts of water vapor and, in relatively cold environments, the temperature of the combustion air may be lowered below the dew point of the combustion air resulting in condensation developing within one or more locations of the engine system, e.g., within components and/or conduits. Condensation may combine with acidic substances within the recirculated exhaust gas, e.g., sulfuric or nitric substances, to form aqueous acids which are typically more corrosive to engine components, especially metal surfaces, than gaseous acids. Additionally, condensation may form water droplets suspended within the combustion air which may impinge one or more surfaces of engine components. As such, the existence of condensation within the engine system may reduce engine system component cycle life, cause premature engine system component failure, and/or undesirably affect engine system performance.

U.S. Pat. No. 6,725,848 ("the '848 patent") issued to Ramamurthy et al. discloses a method of controlling exhaust gas recirculation system based upon humidity. The method of the '848 patent includes sensing a humidity of combustion air within an inlet manifold, of combustion air downstream of a combustion air mixer and upstream of an inlet manifold, or of ambient air. The sensed humidity of the combustion air upstream of the inlet manifold or of the ambient air is correlated with engine speed, engine load, ambient temperature, intake manifold pressure, air/fuel ratio, and the flow rate of recirculated exhaust gas to determine the dew point of the combustion air within the manifold. The method of the '848 patent includes ceasing to recirculate exhaust gas if the sensed humidity within the inlet manifold, as sensed, approaches 100% or if a sensed temperature of the combustion air within the inlet manifold, as correlated, is less than a dew point for the combustion air.

Although the method of the '848 patent may determine if condensation is likely to occur within the inlet manifold as a function of the sensed humidity and may control recirculated exhaust gas as a function thereof, it requires sensing a humidity associated with the exhaust gas recirculation system. Additionally, the apparatus associated with the method of the '848 patent may require a humidity sensor exposed to the combustion air which may potentially decrease the integrity of the inlet manifold or of another component of the exhaust gas recirculation system. Furthermore, the method of the '848 patent only determines the likelihood of condensation within the inlet manifold which may not sufficiently monitor condensation with respect to additional engine system components.

The present disclosure is directed to overcoming one or more of the shortcomings set forth above.

SUMMARY OF THE INVENTION

In one aspect, the present disclosure is directed to a method for operating a virtual dew point sensor with respect to an engine system. The method includes determining a first humidity ratio indicative of the humidity associated with an ambient air as a function of at least a relative humidity associated with the ambient air. The method also includes determining a second humidity ratio indicative of the humidity associated with an exhaust gas as a function of at least one engine parameter. The method also includes determining a third humidity ratio indicative of combustion air directed toward an inlet manifold of an engine as a function of the first and second humidity ratios. The method further includes determining at least one dew point indicative of the combustion air as a function of the third humidity ratio and a pressure indicative of the combustion air.

In another aspect, the present disclosure is directed to a virtual dew point sensor for an engine system having exhaust gas recirculation. The virtual dew point sensor includes first, second, and third sensors respectively configured to establish a signal indicative of a temperature, pressure, and mass flow rate of an exhaust gas directed toward a mixer. The virtual dew point sensor also includes fourth and fifth sensors respectively configured to establish a signal indicative of a temperature and a pressure of ambient air directed toward the mixer. The virtual dew point sensor also includes at least one sixth sensor configured to establish at least one signal indicative of at least one engine parameter. The virtual dew point sensor also includes seventh and eighth sensors respectively configured to establish a signal indicative of a temperature and pressure of an combustion air directed toward an inlet manifold and a controller. The controller is configured to receive a first, a second, a third, a fourth, a fifth, at least one sixth, a seventh, and an eighth input respectively indicative of the first, second, third, fourth, fifth, at least one sixth, seventh, and eighth sensor signals. The controller is also configured to determine a first humidity ratio indicative of the humidity ratio of the combustion air as a function of the first, second, third, fourth, fifth, at least one sixth, and seventh signals and determine at least one dew point of the combustion air as a function of the first humidity ratio and at least one of the fourth or eighth signals.

In yet another aspect, the present disclosure is directed to a method for controlling exhaust gas recirculation with respect to an engine. The method includes determining if a first temperature indicative of a temperature of an inlet gas directed toward an inlet manifold is less than or equal to a first dew point. The first temperature is indicative of a temperature at a first location with respect to the inlet manifold. The method also includes determining if a second temperature indicative of a temperature of an inlet gas directed toward an inlet manifold is less than or equal to a second dew point. The second temperature is indicative of a temperature at a second location with respect to the inlet manifold and the second location is different that the first location. The method further includes reducing an amount of exhaust gas recirculated from downstream of an engine toward a mixer if either of the first or second temperatures is less than or equal to the first and second dew points, respectively.

DETAILED DESCRIPTION

Figure 1:
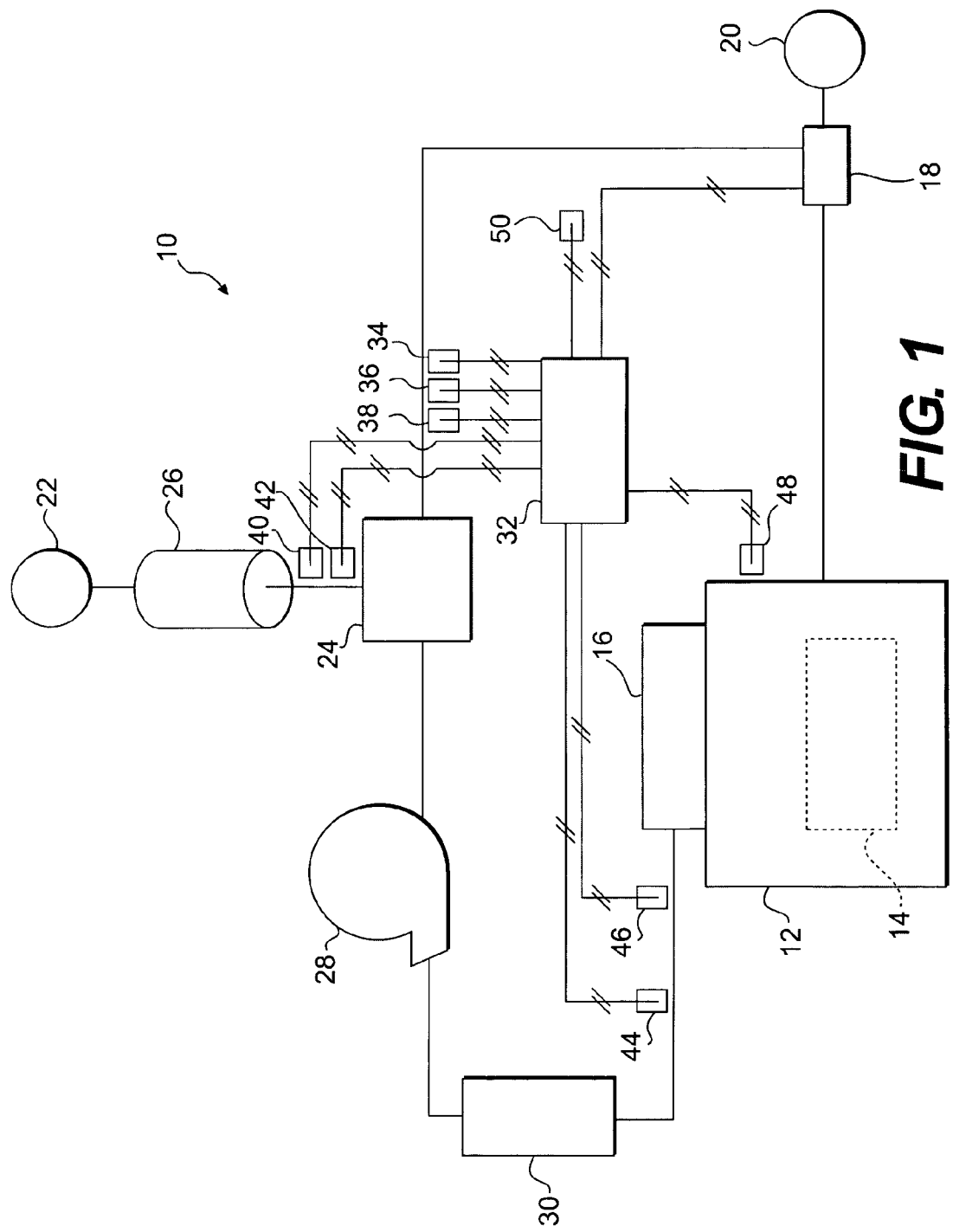
FIG. 1 is a schematic illustration of an exemplary engine system including a virtual dew point sensor in accordance with the present disclosure.

FIG. 1 illustrates an exemplary first engine system 10. First engine system 10 may include an engine 12 having a combustion chamber 14 and an inlet manifold 16. Engine 12 may be configured to transform potential chemical energy, e.g., fuel, into mechanical energy, e.g., torque, via a combustion process, e.g., a two or four cycle piston cylinder combustion arrangement. Exhaust gas may be directed from combustion chamber 14 toward an environment 20 for release thereto. A portion of the exhaust gas may selectively be directed to a mixer 24 via a valve 18. Valve 18 may include a solenoid actuated variable output valve configured to divert a portion of the exhaust gas produced within combustion chamber 14 toward mixer 24. First engine system 10 may also include an air filter 26 configured to filter air received from an environment 22 and direct the filtered air toward mixer 24. Environments 20 and 22 may be the same or different environments and may, for example, include ambient air at any ambient condition. The recirculated exhaust gas, diverted via valve 18, and the filtered air, directed from filter 26, may be combined within mixer 24 to establish combustion air directed toward combustion chamber 14. The combustion air may be compressed via a compressor 28, directed through an air cooler 30 to reduce temperature, directed toward inlet manifold 16, and subsequently communicated to combustion chamber 14. The combustion air may include any type of fluid configured to be directed toward combustion chamber 14, such as, for example, any amounts or proportions of exhaust gas with filtered ambient air, unfiltered ambient air, or enriched air, and may or may not be homogeneously combined with respect to any location between mixer 24 and combustion chamber 14.

It is contemplated that each of the components of first engine system 10 described above may embody and/or include any conventional type of component known in the art, such as, for example, an internal combustion engine, e.g., a gasoline or diesel engine, an air filter including a fibrous fabric particulate filter, a gas mixing device, e.g., a pipe union, a heat exchanger, e.g., an air or liquid cooled heat exchanger, and/or a turbocharged or supercharged compressor system. Accordingly, such components are not described in greater detail. It is also contemplated that first engine system 10 may include any quantity of additional components known in the art, such as, for example, one or more fans (not shown), an exhaust gas cooler, (not shown), an exhaust gas particulate filter (not shown), a muffler (not shown), and/or a catalytic converter (not shown).

First engine system 10 may further include a controller 32 configured to virtually sense dew points within first engine system 10 and further configured to control valve 18 to selectively affect an amount of exhaust gas diverted toward mixer 24. Controller 32 may include one or more microprocessors, a memory, a data storage device, a communications hub, and/or other components known in the art. It is contemplated that controller 32 may be integrated within a general control system capable of controlling additional functions of first engine system 10, e.g., selective control of engine 12, and/or additional systems operatively associated with first engine system 10, e.g., selective control of a transmission system. Controller 32 may be configured to receive input signals from a plurality of sensors 34, 36, 38, 40, 42, 44, 46, 48, 50, perform one or more algorithms to determine appropriate output signals, and may deliver the output signals to valve 18. It is contemplated that controller 32 may receive and deliver signals via one or more communication lines (not referenced) as is known in the art.

Sensors 34, 36, 38, 40, 42, 44, 46, 48, 50 may include any conventional sensor configured to establish a signal indicative of a physical parameter. Specifically, sensor 34 may include a temperature sensor, sensor 36 may include a pressure sensor, and sensor 38 may include a mass flow rate sensor each respectively configured to produce a signal indicative of a temperature, a pressure, and a mass flow rate of the exhaust gas diverted by valve 18 toward mixer 24. Sensor 40 may include a temperature sensor and sensor 42 may include a pressure sensor each respectively configured to produce a signal of a temperature and a pressure of ambient air directed through air filter 26. Sensor 44 may include a temperature sensor and sensor 46 may include a pressure sensor each respectively configured to produce a signal indicative of a temperature and a pressure of the combustion air directed toward inlet manifold 16. Sensor 48 may include one or more sensors each configured to produce one or more signals indicative of various engine parameters, such as, for example, engine speed, fuel rate, coolant temperature, and/or any other parameter known in the art. Sensor 50 may include one or more sensors each configured to produce one or more signals indicative of various parameters of first engine system 10, such as for example, a mass flow rate, e.g., of combustion air directed toward air cooler 30, temperature, e.g., compressor outlet temperature or ambient air temperature, pressure, e.g., ambient air pressure, and/or any other parameter of first engine system 10, as desired. It is contemplated that if first engine system 10 includes an exhaust gas cooler, sensors 34, 36 may be disposed downstream thereof.

Figure 2:
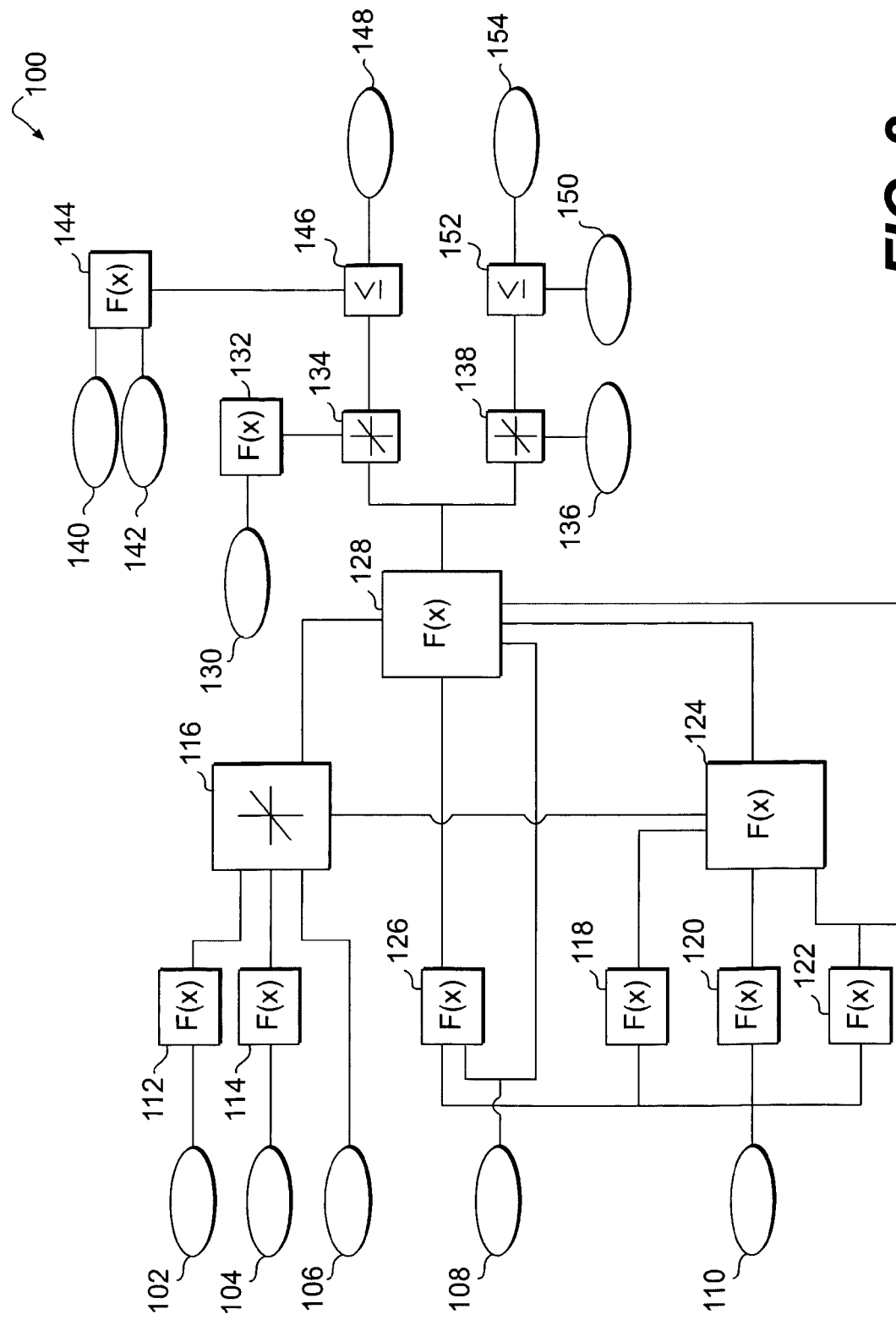
FIG. 2 is a diagrammatic illustration of an exemplary control algorithm configured to be performed by the controller of FIG. 1.

FIG. 2 illustrates an exemplary first control algorithm 100. First control algorithm 100 may be performed by controller 32 to virtually sense first and second dew points and thus the likelihood of condensation within first engine system 10. First control algorithm 100 may determine first and second outputs 148, 154, as a function of the virtually sensed first and second dew points to influence the control and/or operation of valve 18 and, correspondingly, the amount of exhaust gas recirculated toward inlet manifold 16. First control algorithm 100 may include receiving a plurality of inputs, e.g., signals generated by one or more sensors and perform a plurality of functional relations, e.g., algorithms, equations, subroutines, look-up maps, tables, and/or comparisons to influence the operation of valve 18. It is contemplated that first control algorithm 100 may be configured to determine first and second outputs 148, 154 as a function of sensors 34, 36 being disposed downstream of an exhaust gas cooler.

Specifically, first control algorithm 100 may be configured to determine a humidity ratio of the combustion air directed from mixer 24 toward inlet manifold 16 as a function of a relative humidity of ambient air and a relative humidity of an exhaust gas. First control algorithm 100 may include functionally relating one or more sensed parameters, such as, for example, temperatures, pressures, and/or one or more engine parameters to determine the relative humidity of ambient air and the relative humidity of an exhaust gas directed toward mixer 24.

Referring to FIG. 2, inputs 102, 104 may include a signal configured to be indicative of a temperature and pressure of ambient air downstream of air filter 26, respectively, e.g., signals from sensors 40, 42. Input 106 may include a signal configured to be indicative of a relative humidity of the ambient air within environment 22. It is contemplated that input 106 may include a value predetermined and/or estimated to be indicative of the actual relative humidity of the ambient air. For example, input 106 might may be established as a constant value, e.g., 100%, 90%, or 80%, instead of being established via a sensor, to provide conservative and/or non-varying ambient air humidity for subsequent manipulation within one or more functional relations of first control algorithm 100. Input 108 may include a signal indicative of mass flow rate of exhaust gas directed toward mixer 24, e.g., sensor 36. Input 110 may include one or more signals indicative of one or more engine parameters and/or engine system parameters, e.g., signals from sensors 38 and/or 40.

Functional relation 112 may be configured to determine the temperature of ambient air within environment 22, e.g., the ambient air directed toward and through air filter 26, as a function of the filtered air temperature, e.g., input 102. Specifically, functional relation 112 may functionally relate the effects, e.g., heating, air filter 26 may have on the ambient air. For example, functional relation 112 may multiply input 102 by a predetermined factor indicative of an effect air filter 26 may have on the temperature of ambient air directed therethrough. Similarly, functional relation 114 may be configured to determine the pressure of ambient air within environment 22 as a function of the filtered air pressure, e.g., input 104. Specifically, functional relation 114 may functionally relate the effects, e.g., pressure drop, air filter 26 may have on the ambient air. For example, functional relation 114 may multiply input 104 by a predetermined factor indicative of an effect air filter 26 may have on the pressure of ambient air directed therethrough.

Functional relation 116 may be configured to determine a humidity ratio of the ambient air directed from environment 22 through air filter 26 and toward mixer 24. Functional relation 116 may functionally relate the temperature, pressure, and relative humidity of the ambient air, as determined within functional relations 112, 114 and from input 106, with predetermined humidity ratios via one or more relational look-up tables or multi-dimensional maps. For example, functional relation 116 may include a stoichiometric map relating temperature, pressure, and humidity for air.

Functional relations 118, 120, 122 may be configured to determine a mass flow rate of fuel communicated to combustion chamber 14, a water to fuel ratio of exhaust gas produced within combustion chamber 14, and a mass flow rate of ambient air directed toward air filter 26, respectively. Specifically functional relations 118, 120, 122 may functionally relate one or more engine 12 or first engine system 10 parameters, e.g., input 108, with one another and/or predetermined variables or constants within one or more functional relationships, e.g., look-up tables, and/or multi-dimensional maps. For example, functional relation 118 may functionally relate valve timing, throttle, and/or additional parameters, functional relation 120 may functional relate a type of fuel, combustion process data, and/or additional parameters, and functional relation 122 may functionally relate engine speed, displacement, ambient air temperature and pressure, combustion air temperature, and/or additional parameters.

Functional relation 124 may be configured to determine a humidity ratio of the exhaust gas directed from combustion chamber 14 and toward mixer 24. For example, functional relation 124 may functionally relate the mass flow rate of fuel, the water to fuel ratio, the mass flow rate of ambient air, and the humidity ratio of the ambient air within one or more functional relationships, e.g., equations. It is contemplated that functional relation 124 may include a mathematical relationship representative of, for example, $H_{exh}=H_{amb}+(R_{wtf} \times M_{fuel} \times k_1)/M_{amb}$; wherein $H_{exh}$ represents the humidity ratio of the exhaust gas, $H_{amb}$ represents the humidity ratio of the ambient air, $R_{wtf}$ represents the water to fuel ratio, $M_{fuel}$ represents the mass flow rate of fuel, $k_1$ represents a constant, and $M_{amb}$ represents the mass flow rate of the ambient air. It is contemplated that functional relation 114 may include any mathematical relation, e.g., linear or exponential, and that constant $k_1$ may be any suitable constant, e.g., an empirically determined parameter.

Functional relation 126 may be configured to determine the mass flow rate of the combustion air, e.g., the combustion air directed from mixer 24 toward combustion chamber 14, as a function of the mass flow rate of the exhaust gas directed toward mixer 24, e.g., input 108, and one or more engine 12 and/or first engine system 10 parameters, e.g., input 110. Specifically, functional relation 126 may functionally combine the mass flow rate of the ambient air, the mass flow rate of the exhaust gas, and one or more of the effects mixer 24 might have upon the respective flow rates to determine the mass flow rate of the combustion air directed downstream of the mixer. It is contemplated that functional relation 126 may include one or more functional relationships, e.g., look-up tables and/or multi-dimensional maps.

Functional relation 128 may be configured to determine a humidity ratio for the combustion air directed from mixer 24 toward inlet manifold 16. Specifically, functional relation 128 may functionally relate the humidity ratio of the ambient air, the humidity ratio of the exhaust gas, the mass flow rate of the ambient air, and the mass flow rate of the exhaust gas within one or more functional relationships, e.g., equations. It is contemplated that functional relation 128 may include a mathematical relationship representative of, for example, $H_{com}=(H_{exh} \times M_{exh}+H_{amb} \times M_{amb})/M_{com}$; wherein $H_{com}$ is representative of the humidity ratio of the combustion air, $H_{exh}$ is representative of the humidity ratio of the exhaust gas, $M_{exh}$ is representative of the mass flow rate of the exhaust gas, $H_{amb}$ is representative of the humidity ratio of the ambient air, $M_{amb}$ is representative of the mass flow rate of the ambient air, and $M_{com}$ is representative of the mass flow rate of the combustion air. It is also contemplated that functional relation 128 may include any mathematical relation, e.g., linear or exponential, and may include one or more constants.

First control algorithm 100 may also be configured to determine the first and second dew points of the combustion air as a function of the determined humidity ratio of the combustion air and one or more pressures. First control algorithm 100 may also be configured to functionally relate the first and second dew points with one or more temperatures and determine if the first and second dew points are less than or equal to the temperatures.

Again referring to FIG. 2, input 130 may be configured to be indicative of a pressure of the exhaust gas directed toward mixer 24, e.g., a signal from sensor 38. Functional relation 132 may be configured to determine the pressure of the combustion air directed from mixer 24 as a function of the exhaust gas pressure. Specifically, functional relation 132 may functionally relate the effects, e.g., pressure drop of mixer 24 and/or pressure balance with the ambient air, that may affect pressure of the exhaust gas to determine the pressure of the combustion air. For example, functional relation 132 may determine the combustion air pressure downstream of the mixer and upstream of the compressor. Functional relation 134 may be configured to determine the first dew point of the combustion air with respect to the combustion air pressure determined from functional relation 132. Specifically, functional relation 134 may determine the first dew point, e.g., an combustion air dew point downstream of mixer 24 and upstream of compressor 28, as a function of an combustion air humidity ratio, an combustion air pressure, and one or more look-up tables and/or multi-dimensional maps, e.g., a stoichiometric map relating temperatures, pressures, and humidity for combustion air.

Input 136 may be configured to be indicative of a pressure of the combustion air directed toward combustion chamber 14, e.g. a signal from sensor 46. Similarly to functional relation 134, functional relation 138 may be configured to determine the second dew point of the combustion air with respect to the combustion air pressure established by input 136. For example, functional relation 138 may determine the second dew point, e.g., a combustion air dew point upstream of combustion chamber 14, as a function of a combustion air humidity ratio, a combustion air pressure, and one or more look-up tables and/or multi-dimensional maps, e.g., a stoichiometric map relating temperatures, pressures, and humidity for combustion air. It is contemplated that functional relation 138 may determine the second dew point indicative of a dew point of combustion air within combustion chamber 14 as a function of input 136 being indicative of a pressure of combustion air within combustion chamber 14 and/or control algorithm 100 may include an additional functional relation (not shown) configured to determine the pressure of combustion air within combustion chamber 14 as a function of the pressure of the combustion chamber directed toward inlet manifold 16.

Inputs 140, 142 may be configured to be indicative of respective temperatures of the exhaust gas and the ambient air directed toward mixer 24, e.g., respective signals from sensors 34, 40. Functional relation 144 may be configured to functionally relate the exhaust gas and ambient air temperatures to determine a first temperature indicative of the combustion air downstream of mixer 24, e.g., a temperature of the combustion air that corresponds to the combustion air pressure determined within functional relation 132. Similarly, input 150 may be configured to be indicative of a second temperature indicative of a temperature of combustion air downstream of air cooler 30 and upstream of manifold 16, e.g., a temperature of combustion air that corresponds to the combustion air pressure determined from input 136. It is contemplated that the temperature indicative of the combustion air downstream of mixer 24 may, alternatively, be determined by an appropriately disposed temperature sensor (not shown) similar to input 150.

Functional relations 146, 152 may each be configured to compare a respective one of first and second dew points to establish first and second outputs 148, 154 as a function thereof. Specifically, functional relation 146 may compare the first dew point, as determined within functional relation 134, with the first combustion air temperature, as determined within functional relation 144, to determine if the first dew point is greater than the first combustion air temperature. Similarly, functional relation 152 may compare the second dew point, as determined within functional relation 138, with the second combustion air temperature, as determined from input 150, to determine if the second dew point is greater than the second combustion air temperature. For example, if the first inlet manifold temperature is less than or equal to first dew point, output 148 may be configured to, via controller 32, limit or discontinue exhaust gas recirculation by, for example, influencing valve 18 to close. Also, if the first inlet manifold temperature is greater than first dew point, first output 148 may be configured to not, via controller 32, limit or discontinue exhaust gas recirculation. Second output 154 may be similarly determined as first output 148. It is contemplated that first and second outputs 148, 154 may be configured as a flag criteria and, as such, may be configured to only limit or discontinue exhaust gas recirculation when a combustion air temperature is less than or equal to a determined dew point. It is also contemplated that functional relations 146, 152 may or may not include a margin of error factor, e.g., a percentage or fixed value increase to account for mathematical rounding discrepancies and/or other computational inaccuracies as is known in the art. As such, controller 32, sensors 34, 36, 38, 40, 42, 44, 46, 48, 50, and, in particular first control logic 100, may virtually sense dew points with respect to first engine system 10 and/or components thereof and influence control of first engine system 10 to limit or discontinue the recirculation of exhaust gas when condensation may be likely to occur therein. It is further contemplated that if functional relation 138 is configured to determine a dew point of the combustion air within combustion chamber 14, input 150 may be indicative of a temperature of combustion air within combustion chamber 14 and functional relation 152 may be configured to compare the second combustion air temperature with the second dew point to determine if the second dew point is greater than the second combustion air temperature. As such, control algorithm 100 may, alternatively, be configured to determine second output 154 as a function of a dew point and corresponding temperature of combustion air within combustion chamber 14.

Figure 3:
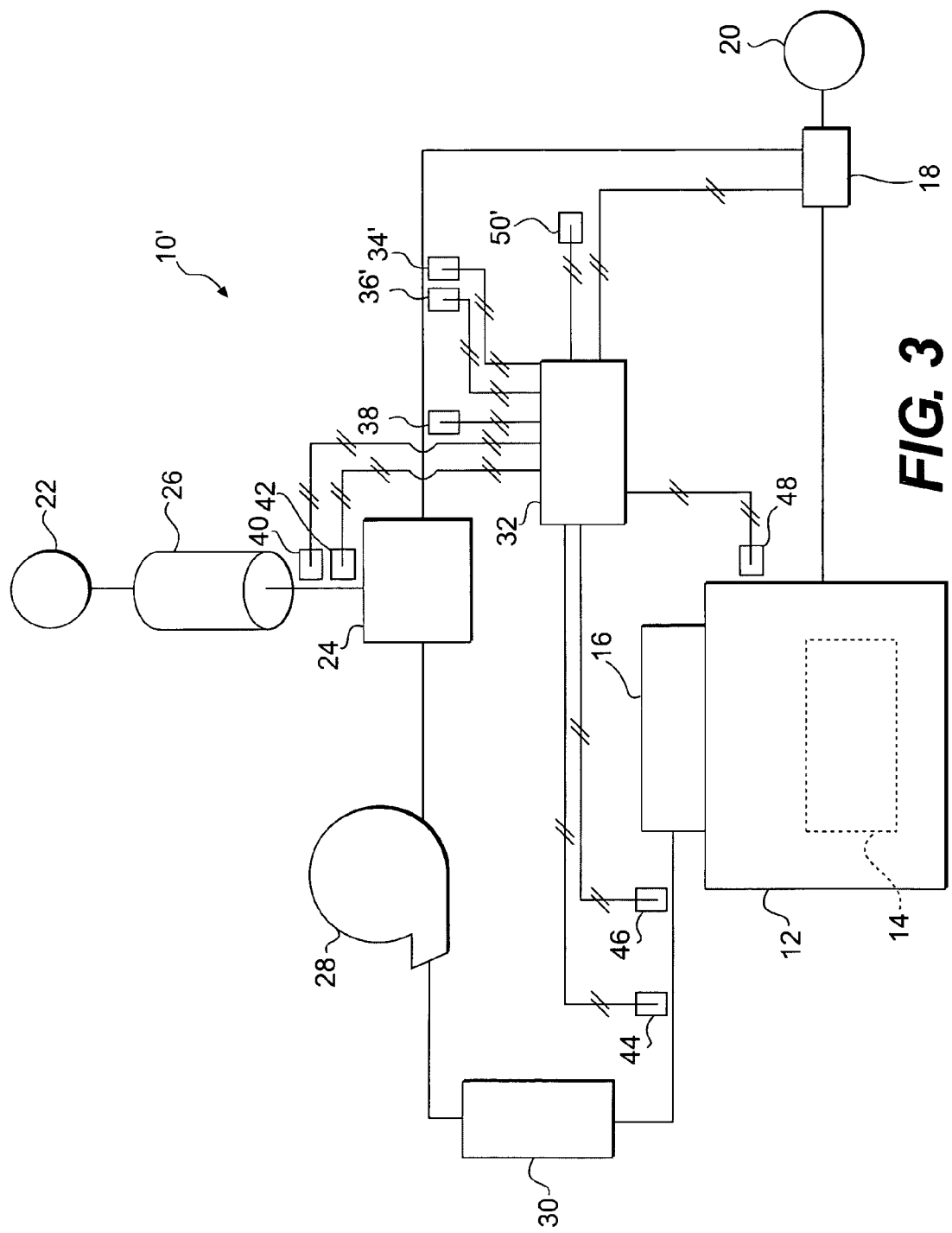
FIG. 3 is a schematic illustration of another exemplary engine system including a virtual dew point sensor in accordance with the present disclosure.

FIG. 3 illustrates an exemplary second engine system 10'. Second engine system 10' is substantially similar to first engine system 10 and, as such, only the differences are described below.

Second engine system 10' may include sensors 34', 36', 50' each configured to establish a signal indicative of a physical parameter. Specifically, sensor 34' may include a temperature sensor and sensor 36' may include a pressure sensor each respectively configured to produce a signal indicative of a temperature and a pressure of the exhaust gas diverted by valve 18 toward mixer 24. Sensor 50' may include one or more sensors each configured to produce one or more signals indicative of various parameters of second engine system 10', such as, for example, any of the parameters sensed by sensor 50 with respect to first engine system 10, inlet coolant temperature, e.g., an inlet water temperature of a water cooled exhaust gas cooler, an engine speed, e.g., revolutions per minute, an engine load, and/or any other parameter, as desired. It is contemplated that if second engine system 10' includes an exhaust gas cooler, sensors 34', 36' may be disposed upstream of thereof. It is also contemplated that if second engine system 10' includes an exhaust gas cooler, sensor 38, may or may not be disposed downstream thereof.

Figure 4:
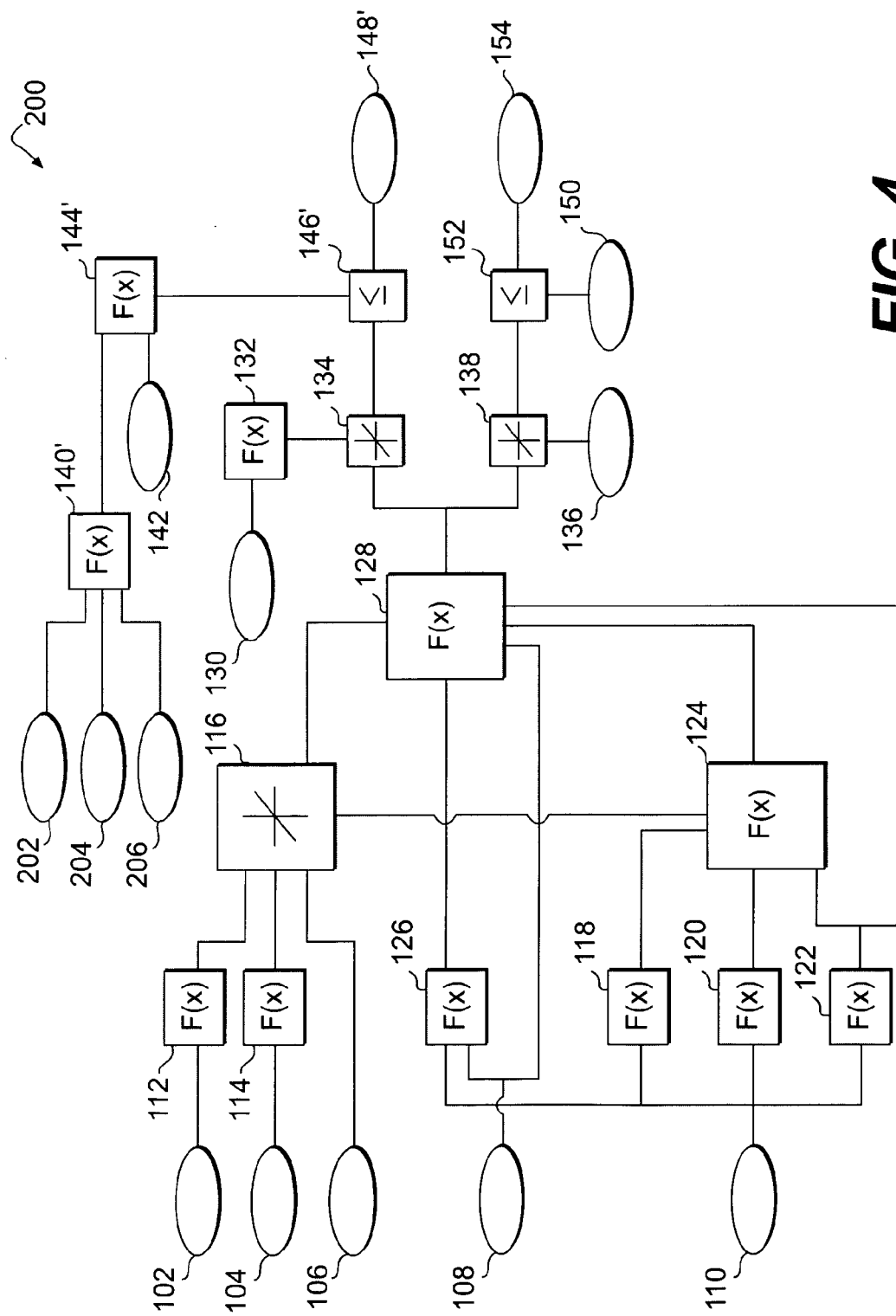
FIG. 4 is a diagrammatic illustration of another exemplary control algorithm configured to be performed by the controller of FIG. 3.

FIG. 4 illustrates an exemplary second control algorithm 200. Second control algorithm 200 may be performed by controller 32 to virtually sense first and second dew points and thus the likelihood of condensation within second engine system 10'. Second control algorithm 200 may be substantially similar to first control algorithm 100 and, as such, only the differences will be described below. Second control algorithm 200 may determine first and second outputs 148', 154, as a function of the virtually sensed first and second dew points to influence the control and/or operation of valve 18 and, correspondingly, the amount of exhaust gas recirculated toward inlet manifold 16. Second control algorithm 200 may include receiving a plurality of inputs, e.g., signals generated by one or more sensors, perform a plurality of functional relations, e.g., algorithms, equations, subroutines, look-up maps, tables, and/or comparisons, and establish one or more outputs to affect the operation of valve 18. It is contemplated that second control algorithm 200 may be configured to determine first and second outputs 148', 154 as a function of sensors 34', 36' being disposed upstream of an exhaust gas cooler.

Referring to FIG. 4, inputs 202, 204, 206 may be configured to be respectively indicative of a temperature of exhaust gas directed toward mixer 24, e.g., a signal from sensor 34', an engine speed, e.g., revolutions per minute of an engine drive shaft, and a temperature of a coolant for an exhaust gas cooler, e.g., an inlet water temperature for a water cooled exhaust gas cooler. Similar to first control algorithm 100, functional relation 144' may be configured to functionally relate the exhaust gas temperature, engine speed, coolant temperature, and the ambient air temperature to determine a first temperature indicative of the combustion air downstream of mixer 24, e.g., a temperature of the combustion air that corresponds to combustion air pressure determined within functional relation 132. It is contemplated that functional relation 144' may be configured to functionally determine the effects an exhaust gas cooler may have on the temperature of the exhaust gas and that such effects may vary as a function of engine parameters, e.g., a temperature of a coolant may increase as a function of increased engine loads. It is also contemplated that the coolant temperature may be a signal from one of sensors 50' and/or may include a functional relation determining the coolant temperature as a function of, for example, a temperature of coolant water associated with engine 12.

Functional relation 146' may be configured to compare the first dew point to establish first output 148' as a function thereof. Similarly to functional relation 146, functional relation 146' may compare the first dew point, as determined within functional relation 134, with the first combustion air temperature, as determined within functional relation 144', to determine if the first dew point is greater than the first combustion air temperature. For example, if the first combustion air temperature is less than or equal to the first dew point, output 148' may be configured to, via controller 32, limit or discontinue exhaust gas recirculation by, for example, influencing valve 18 to close. Additionally, if the first combustion air temperature is greater than the first dew point, first output 148' may be configured to not, via controller 32, limit or discontinue exhaust gas recirculation. It is contemplated that first output 148' may be configured as a flag criteria and, as such, may be configured to only limit or discontinue exhaust gas recirculation when a combustion air temperature is less than or equal to a determined dew point. It is also contemplated that functional relation 146' may or may not include a margin of error factor, e.g., a percentage or fixed value increase to account for mathematical rounding discrepancies and/or other computational inaccuracies as is known in the art. As such, controller 32, sensors 34', 36', 38, 40, 42, 44, 46, 48, 50', and, in particular second control logic 200, may virtually sense dew points with respect to second engine system 10' and/or components thereof and affect control of second engine system 10' to limit or discontinue the recirculation of exhaust gas when condensation may be likely to occur therein.

It is contemplated that any inputs of first and second control algorithms 100, 200 may embody any signal, such as, for example, a pulse, a voltage level, a magnetic field, a sound or light wave, and/or other signal format known in the art. It is also contemplated that any functional relations of first and second control algorithms 100, 200 may include any look-up table, multi-dimensional map, equation, formula, subroutine, algorithm, any other functional relation known in the art, and/or combination thereof.

INDUSTRIAL APPLICABILITY

The disclosed virtual dew point sensor may be applicable for predicting the formation of condensation with respect to any engine system including exhaust gas recirculation. The disclosed virtual dew point sensor may predict when formation of condensation upstream of a compressor and downstream of a combustion air cooler is likely to occur and may allow a controller to limit or discontinue an amount of exhaust gas recirculated into the combustion air as a function thereof. The operation of first and second engine systems 10, 10' and, in particular, first and second control algorithms 100, 200 will be explained below.

First and second engine systems 10, 10' may each be associated with and configured to provide power to a mobile vehicle, a marine vessel, and/or a generator. As such first and second engine systems 10, 10' may operate in varying and different environments, including, for example, relatively cold climates, e.g., climates having a relatively low temperature of ambient air. It is noted that the ambient air in cold climates typically includes small amounts of water vapor because of the affects of the dew point, as is known in the art, however, exhaust gas produced as a by-product of a combustion process may include considerable amounts of water vapor. It is also noted that if a temperature of a gas that includes water vapor suspended therein decreases below a dew point associated with the gas, condensation may occur. Condensation may form water droplets suspended within the gas and, if the gas contains acidic substances, e.g., exhaust gas that may contain gaseous sulfuric and nitric acids, the acidic substances may combine with the condensation to form aqueous acidic substances.

Referring to FIGS. 1 and 3, combustion air directed toward manifold 16 may include considerable amounts of water vapor and depending upon the temperature of the combustion air, as affected by, for example, air cooler 30, ambient air temperature, and/or exhaust gas air temperature, condensation may form. Reducing the formation of water droplets within the combustion air may be desired, for example, so as to reduce water droplets impinging and potentially damaging one or more engine components, e.g., one or more blades of compressor 28. As such, it may be desirable to determine if condensation is likely to occur upstream of compressor 28 and, if so, control the recirculation of exhaust gas to reduce the potential of condensation. Reducing the formation of aqueous acids within the combustion air may be desired so as to reduce corrosive substances from corroding and potentially damaging one or more engine components, e.g., inlet manifold 16 and/or one or more air inlet valves associated with combustion chamber 14.

Accordingly, controller 32 may receive a plurality of inputs from one or more of sensors, e.g., sensors 34, 34', 36, 36', 38, 40, 42, 44, 46, 48, 50, and/or 50', perform one or more algorithms, e.g., first control algorithm 100, second control algorithm 200, and/or additional algorithms, and may output a control signal to valve 18. It is contemplated that the additional algorithms may be configured to determine operational output signals to control valve 18, e.g., affect the degree and/or timing of the opening and/or closing of valve 18, as a function of one or more parameters of engine 12, first and second engine systems 10, 10' and/or predetermined or desired relationships. As such, first and/or second control algorithms 100, 200 may be integrated, e.g., as an input or a subroutine, within one or more of the additional algorithms, performed independently of the additional algorithms, and/or configured to limit exhaust gas recirculation by manipulating, e.g., overriding, an operational control signal for valve 18. It is also contemplated that first and second control algorithms 100, 200 may prohibit exhaust gas recirculation by prohibiting valve 18 from opening, e.g., prohibiting controller 32 from communicating an output signal to valve 18 to move valve 18 from a closed position toward an open position, and may discontinue gas recirculation by moving valve 18 toward a closed position, e.g., affecting controller 32 to communicate an output signal to valve 18 to move valve 18 from an open position toward a closed position. It is contemplated that the additional algorithms configured to affect movement of valve 18 may determine an output signal as a function of any desired parameter, e.g., a parameter of engine 12, first and second engine systems 10, 10', and/or a predetermined relationship.

Referring to FIGS. 2 and 4, first and second control algorithms 100, 200 may determine a humidity ratio for the combustion air directed toward inlet manifold 16 (FIGS. 1 and 3) as a function of a determined humidity ratio of an ambient air and a determined humidity ratio of an exhaust gas. First and second dew points of the combustion air may be determined as a function of the combustion air humidity ratio and one or more pressures indicative of pressures of combustion air with respect to particular locations within first and second engine systems 10, 10', e.g., upstream of compressor 28 or downstream of air cooler 30. The first and second dew points may be functionally related with temperatures of combustion air corresponding to the particular locations within first and second engine systems 10, 10' associated with the one or more pressures. First and second control algorithms 100, 200 may determine appropriate outputs 148, 148', 154 as a function of a comparison between respective combustion air temperatures and the first and second dew points, to control the amount of recirculated exhaust gas which may reduce the formation of condensation within first and second engine systems 10, 10'.

It is contemplated that the functional relations of first and second control algorithms 100, 200 may be performed in any order and are described herein with a particular order for exemplary purposes only. It is also contemplated that first and second control algorithms 100, 200 may be performed continuously, periodically, with or without a uniform frequency, and/or singularly. It is further contemplated that first and second control algorithms 100, 200 may respectively include a decision step (not shown) configured to determine whether first and second control algorithms 100, 200 should be performed, e.g., determine if the ambient temperature is below a predetermined temperature estimated to be indicative of a threshold above which condensation is unlikely to occur. For example, such a decision step may decide that first and second control algorithms 100, 200 may not need to be performed because the ambient air temperature is significantly above a dew point, e.g., engine system 10 is not operated within a relatively cold climate.

Because first and second control algorithms 100, 200 virtually determine a dew point with respect to predetermined locations associated with an engine system, the integrity of one or more engine system components may be preserved. Additionally, by controlling the recirculation of exhaust gas as a function of the virtually determined dew points, first and second control algorithms 100, 200 may reduce the formation of water droplets and/or aqueous acids and thus may reduce adverse effects of impact erosion and/or corrosion within first and second engine systems 10, 10' and/or within one or more components thereof.

It will be apparent to those skilled in the art that various modifications and variations can be made to the disclosed system for a virtual dew point sensor. Other embodiments will be apparent to those skilled in the art from consideration of the specification and practice of the disclosed method and apparatus. It is intended that the specification and examples be considered as exemplary only, with a true scope being indicated by the following claims and their equivalents.

What is claimed is:

1. A method for operating a virtual dew point sensor with respect to an engine system comprising:
   determining a first humidity ratio indicative of the humidity associated with an ambient air as a function of at least a relative humidity associated with the ambient air;
   determining a second humidity ratio indicative of the humidity associated with an exhaust gas as a function of at least one engine parameter;
   determining a third humidity ratio indicative of combustion air directed toward an inlet manifold of an engine as a function of the first and second humidity ratios; and
   determining at least one dew point indicative of the combustion air as a function of the third humidity ratio and a pressure indicative of the combustion air.

2. The method of claim 1, wherein the pressure indicative of the combustion air is a pressure indicative of the combustion air downstream of an air cooler and upstream of a combustion air manifold.

3. The method of claim 1, wherein the pressure indicative of the combustion air is a pressure indicative of the combustion air downstream of a mixer and upstream of a compressor.

4. The method of claim 1, wherein determining the second humidity ratio includes functionally relating at least one of a mass flow rate of fuel directed toward a combustion chamber of the engine, a mass flow rate of ambient air directed toward a mixer, a mass flow rate of exhaust gas directed toward the mixer, or a predetermined parameter indicative of a water to fuel ratio of the exhaust gas.

5. The method of claim 1, wherein determining the third humidity ratio further includes functionally relating at least one of a mass flow rate of combustion air directed toward the inlet manifold, or a mass flow rate of ambient air directed toward the inlet manifold.

6. The method of claim 1, wherein the relative humidity associated with the ambient air is a predetermined value indicative of an estimated relative humidity of the ambient air.

7. A virtual dew point sensor for an engine system having exhaust gas recirculation comprising:
- first, second, and third sensors respectively configured to establish a signal indicative of a temperature, pressure, and mass flow rate of an exhaust gas directed toward a mixer;
- fourth and fifth sensors respectively configured to establish a signal indicative of a temperature and a pressure of ambient air directed toward the mixer;
- at least one sixth sensor configured to establish at least one signal indicative of at least one engine parameter;
- seventh and eighth sensors respectively configured to establish a signal indicative of a temperature and pressure of combustion air directed toward an inlet manifold; and
- a controller configured to:
    - receive a first, a second, a third, a fourth, a fifth, at least one sixth, a seventh, and an eight input respectively indicative of the first, second, third, fourth, fifth, at least one sixth, seventh, and eighth sensor signals,
    - determine a first humidity ratio indicative of the humidity ratio of the combustion air as a function of the first, second, third, fourth, at least one sixth, and seventh signals, and
    - determine at least one dew point of the combustion air as a function of the first humidity ratio and at least one of the fourth or eighth signals.

8. The virtual dew point sensor of claim 7, wherein:
- the at least one dew point includes first and second dew points, the first dew point indicative of a dew point of the combustion air upstream of a compressor and the second dew point indicative of a dew point of the combustion air upstream of a combustion chamber; and
- the controller is further configured to:
    - compare the first dew point with a temperature indicative of the combustion air upstream of the compressor, and
    - compare the second dew point with a temperature indicative of the combustion air upstream of the combustion chamber.

9. The virtual dew point sensor of claim 7, wherein:
- the at least one sixth sensor includes a plurality of sixth sensors;
- each of the plurality of sixth sensors configured to produce a signal indicative of an engine parameter; and
- the plurality of sixth sensors configured to produce signals indicative of at least one of an engine speed, an air/fuel ratio, and a valve timing.

10. The virtual dew point sensor of claim 9, wherein the controller is further configured to determine at least one of a mass flow rate of fuel, a water to fuel ratio, or a mass flow rate of ambient air as a function of the signals of the plurality of sixth sensors.

11. The virtual dew point sensor of claim 7, wherein the controller is further configured to:
- determine a first output as a function of the first humidity ratio, the first output configured to affect control of a valve configured to direct the exhaust gas toward the mixer.

12. The virtual dew point sensor of claim 7, wherein the controller is configured to determine the first humidity as a function of a second humidity indicative of a humidity of the ambient air and a third humidity indicative of a humidity of the exhaust gas.

13. The virtual dew point sensor of claim 12, wherein the controller is configured to determine the second humidity as a function of the fourth signal, the at least one sixth signal, and an estimated relative humidity of the ambient air.

14. The virtual dew point sensor of claim 12, wherein the controller is configured to determine the third humidity as a function of the first, second, third, and at least one sixth signals.

15. A method for controlling exhaust gas recirculation with respect to an engine comprising:
- determining if a first temperature indicative of a temperature of an inlet gas directed toward an inlet manifold is less than or equal to a first dew point, the first temperature indicative of a temperature at a first location with respect to the inlet manifold;
- determining if a second temperature indicative of a temperature of an inlet gas directed toward the inlet manifold is less than or equal to a second dew point, the second temperature indicative of a temperature at a second location with respect to the inlet manifold, the second location being different that the first location; and
- reducing an amount of exhaust gas recirculated from downstream of the engine toward a mixer if either of the first or second temperatures is less than or equal to the first and second dew points, respectively.

16. The method of claim 15, wherein the first location is disposed downstream of a mixer and upstream of a compressor.

17. The method of claim 15, further including:
- determining a first humidity ratio indicative of a humidity of ambient air directed toward the mixer as a function of an estimated relative humidity of the ambient air;
- determining a second humidity ratio indicative of a humidity of exhaust gas directed toward the mixer as a function of a plurality of engine parameters sensed by a plurality of sensors; and
- determining a third humidity ratio as a function of the first humidity ratio, the second humidity ratio, a mass flow rate of the exhaust gas, and a mass flow rate of the ambient air.

18. The method of claim 17, further including:
- determining the mass flow rate of the exhaust gas by sensing the mass flow rate of the exhaust gas upstream of the mixer; and
- determining the mass flow rate of the ambient air as a function of at least one sensed engine parameter.

19. The method of claim 15, further including determining the first and second dew points as function of an estimated relative humidity of the ambient air and a functionally determined water to fuel ratio of combustion of the exhaust gas.

20. The method of claim 15, further including determining the first and second dew points as a function of a single relative humidity value wherein the single relative humidity value is an estimated relative humidity value indicative of a relative humidity of the ambient air.

* * * * *